US006635878B2

(12) United States Patent
Bertelsen

(10) Patent No.: US 6,635,878 B2
(45) Date of Patent: Oct. 21, 2003

(54) GAMMA CAMERA WITH AUTOMATIC ADJUSTMENT OF THE ENERGY SPECTRUM

(75) Inventor: Hugo Bertelsen, Aalborg (DK)

(73) Assignee: Koninklijke Philips Electronics N.V., Eindhoven (NL)

(*) Notice: Subject to any disclaimer, the term of this patent is extended or adjusted under 35 U.S.C. 154(b) by 207 days.

(21) Appl. No.: 09/881,977

(22) Filed: Jun. 13, 2001

(65) Prior Publication Data

US 2003/0042423 A1 Mar. 6, 2003

(51) Int. Cl.[7] .............................................. G01T 1/208
(52) U.S. Cl. .................... 250/369; 250/362; 250/363.09
(58) Field of Search ............................ 250/361 R, 362, 250/363.07, 363.09, 369, 370.01, 370.11, 370.08, 370.09, 371

(56) References Cited

U.S. PATENT DOCUMENTS 4,661,909 A * 4/1987 Kumazawa et al. ........ 364/414
5,677,536 A    10/1997 Vickers

* cited by examiner

Primary Examiner—Constantine Hannaher
Assistant Examiner—Timothy Moran
(74) Attorney, Agent, or Firm—Eugene E. Clair

(57) ABSTRACT

A nuclear camera system is provided in which the energy spectrum peaks identified by a camera detector head are automatically adjusted to account for drift and other sources of inaccuracy. Histograms of events detected by the photo-multiplier tubes of the detector head are acquired continuously and updated periodically. A system operator initiates the adjustment with an autopeaking command which causes the system to ascertain the validity of the histogram data and, if it is valid, to determine a peak energy level. The determined level is compared to a theoretical value for an isotope present and the comparison is used to adjust the gain applied to energy data of the detector head.

19 Claims, 4 Drawing Sheets

GAMMA CAMERA WITH AUTOMATIC ADJUSTMENT OF THE ENERGY SPECTRUM

This invention relates to gamma cameras used for medical nuclear imaging and, in particular, to gamma cameras with automatic adjustment of the detected energy spectrum.

Gamma cameras are widely used to make images of the interior of the body by detecting emissions of radioisotopes injected into a patient's body. The detector or detectors of a gamma camera are highly sensitive to radioisotope emissions, as they must be able to detect the energy level of an emission event as well as the precise location of the event. Consequently virtually all gamma cameras have procedures for calibrating the detectors. Usually this is done with a source of radiation that floods the detectors with a known level of radiation. Detector gain circuits and/or correction tables are then adjusted to align the outputs of the photomultiplier tubes (PMTs) to the known radiation us level.

However, the characteristics of the detectors can drift continuously even during the course of an imaging procedure. These variations are due to factors such as temperature changes, magnetic field variation, and PMT drift. One approach to dealing with this continuous drift is described in U.S. Pat. No. 5,677,536, where histograms of each PMT are sampled each time the number of scintillation events reaches a predetermined count, and the PMT gain or calibration tables for each PMT is adjusted following each sampling time. These corrections are performed "on the fly" during operation of the camera, and run continuously while the camera is being used. A less complex approach is to analyze the histogram for the current location of the peak energy value, then adjust the energy window for that peak to be centered around the current peak energy value. However, these approaches are very processing intensive, imposing significant operating overhead on the camera system, and the window adjustment approach is distressing to clinicians who expect a physical constant to remain so. Accordingly it is desirable to be able to adjust a gamma camera for drift without the foregoing drawbacks.

In accordance with the principles of the present invention, the detector of a gamma camera is automatically adjusted for drift and other factors producing an unwanted shift of the energy spectrum peak. A histogram of event data is continuously acquired and updated while the camera is in use. Upon receipt of a command to perform autopeaking, recently acquired event data is analyzed to determine if a valid energy histogram is present. This analysis may comprise steps such as determining if a minimum number of counts have been recorded, examining the signal-to-noise ratio of the photopeak, and analyzing the ratio of counts inside an energy window to the counts outside the window. The system is informed of the identity of the isotopes being used so that a check can be made of the acquired data to expected values. When a valid histogram is present, the system determines the peak value of the photopeak, and then computes a gain correction factor based upon the relation of the measured peak to the theoretical peak value for the isotopes present. The gain correction factor is applied to all energy values, thereby providing a correction for all photopeaks of all isotopes present.

Figure 1:
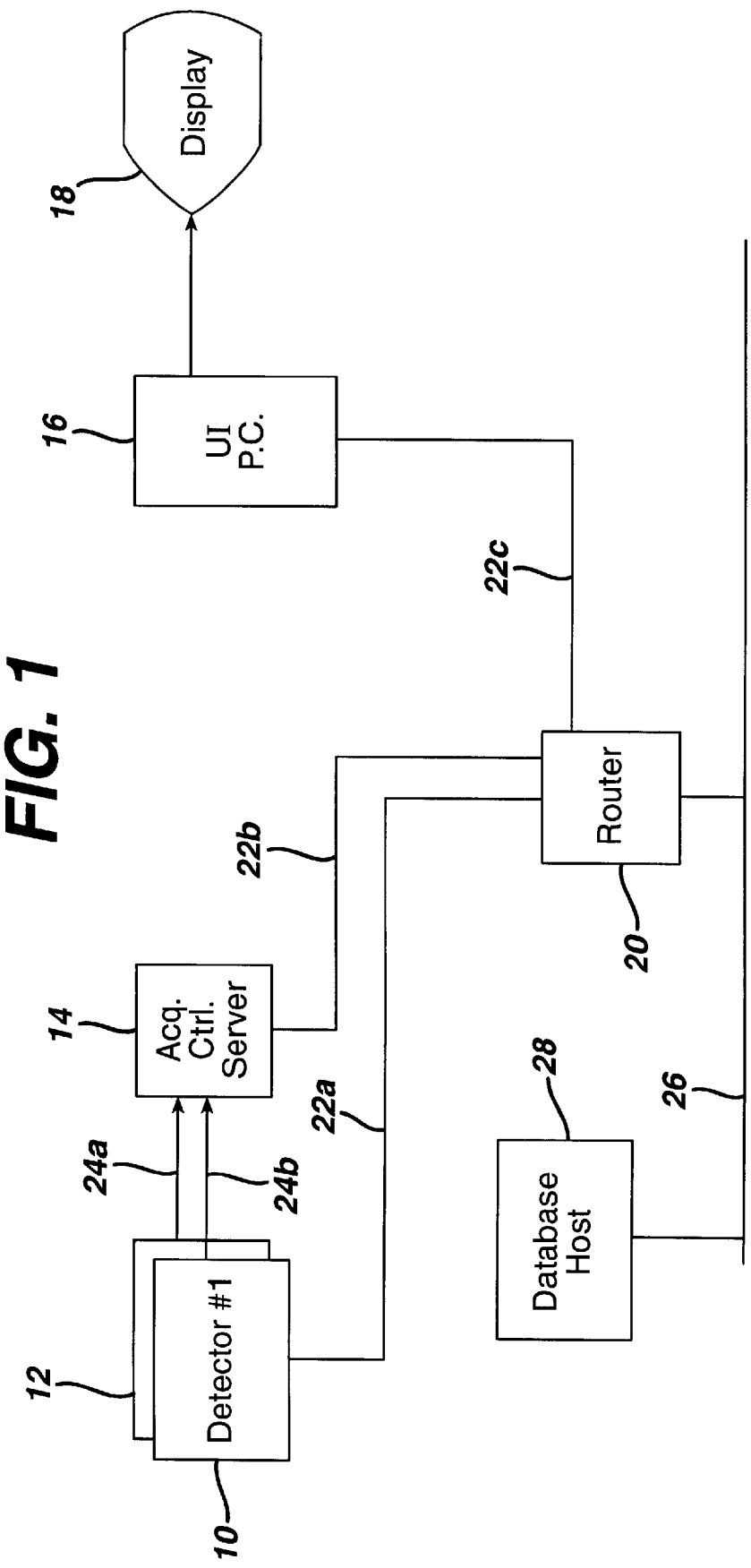
FIG. 1 illustrates in block diagram form a gamma camera constructed in accordance with the principles of the present invention.

Referring first to FIG. 1, a gamma camera constructed in accordance with the principles of the present invention is shown in block diagram form. The present invention may be used with either a single detector gamma camera, or with a dual detector gamma camera such as those shown in U.S. Pat. Nos. 5,760,402 (Hug. et al.) or 6,150,662 (Hug et al.). The dual detector cameras shown in these patents are commercially available as the Forte™ and Skylight™ gamma cameras from ADAC Laboratories of Milpitas, Calif. These camera systems include one or more detectors 10, 12 which sense scintillation events and transfer event data over a high speed serial bus 24a, 24b from each detector to an acquisition control server 14. The acquisition control server 14 bins the event data into images, which are then sent by way of a router 20 to a database host 28 connected to a department Ethernet 26. The database host 28 is the computer on which the acquired images are normally saved. The database host is also the processing and viewing station where 3D reconstruction, re-slicing and presentation of the processed images to the user is performed. The router 20 serves to isolate internal camera data traffic from more varied departmental data traffic. A user interface personal computer 16 is coupled to the acquisition portion of the gamma camera by the router 20 and an Ethernet network 22a, 22b, 22c. The p.c. 16 controls and monitors the image data acquisition and may perform additional image processing and display functions using an image display 18. P-scope and energy spectrum data may be displayed to the user on the display 18, enabling the user to position the patient properly in front of the camera, set energy windows correctly, and review acquired data, for instance.

Figure 2:
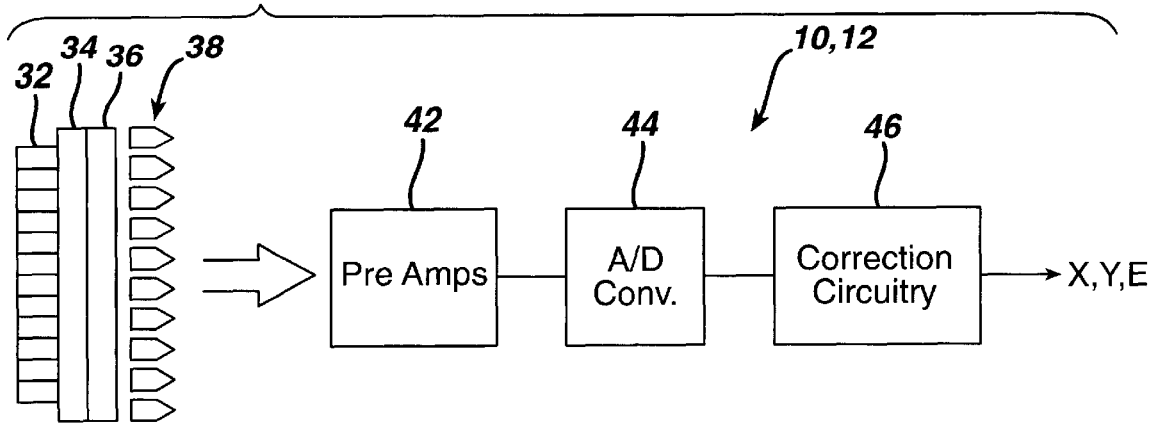
FIG. 2 illustrates the detector of a gamma camera in block diagram form.

A camera detector is shown in greater detail in FIG. 2. As is well known in the art, a gamma camera detector is composed of a collimator 32, a scintillation crystal 34, and a lightguide 36. The photons produced by the crystal 34 and guided through the lightguide 36 are received by an array of photomultiplier tubes (PMTs) 38. A scintillation event is usually received over an area covering several PMTs, and the outputs of the tubes are sensed and used to locate the position on the detector at which the radiation event was received. The PMT output signals are amplified by pre-amplifiers 42 and digitally sampled by A/D converters 44. The samples from each PMT are accumulated for the duration of a scintillation event and, since multiple PMT's are involved in the detection of a single event, the accumulated outputs of multiple PMS's are accumulated to acquire the overall energy signal for a particular scintillation event. The detected energy data and location data from each scintillation event is modified by correction circuitry 46, which produces the detector outputs for energy (E) and event location (X,Y).

Figure 3A:
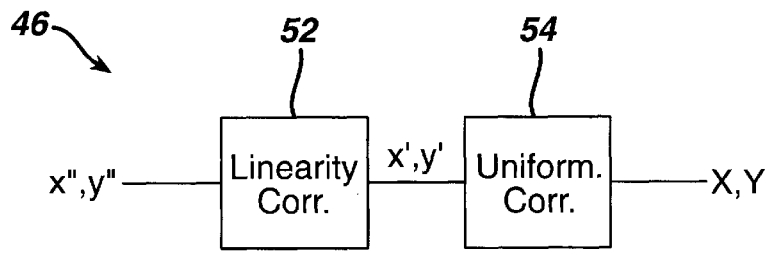
FIGS. 3a and 3b illustrate details of the correction circuitry of the detector of FIG. 2 which operate to adjust the energy spectrum peak in accordance with the principles of the present invention.
Figure 3B:
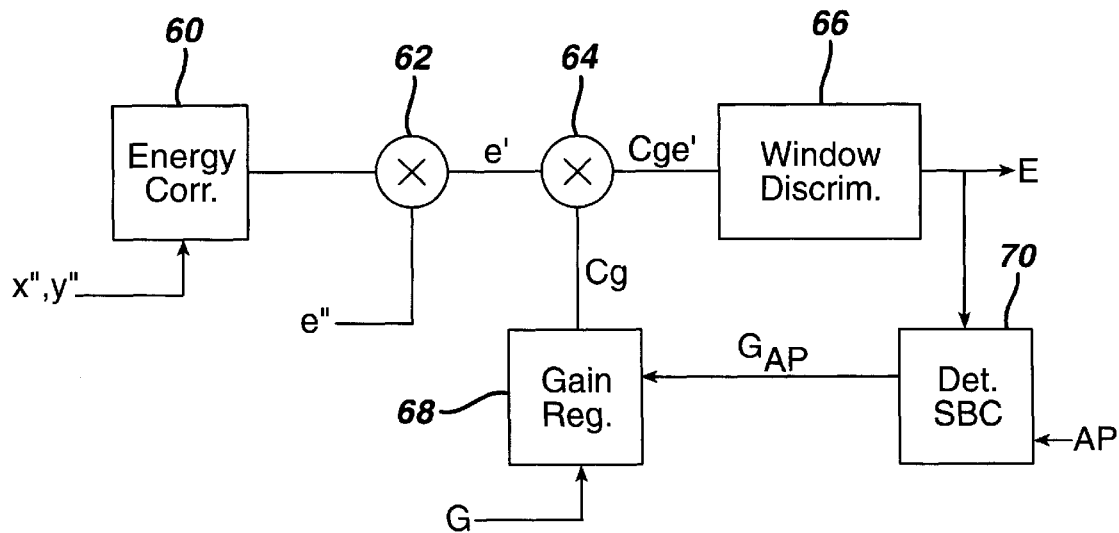

Details of the correction circuitry 46 of FIG. 2 are shown in FIGS. 3a and 3b. The x,y position data is corrected for nonlinearity and nonuniformity as illustrated in FIG. 3a. The raw x",y" position data undergoes processing by a linearity corrector 52 to produce partially corrected location data x',y', which then undergoes processing by a uniformity corrector 54. The corrected location data X,Y is produced at the output of the detector 10,12 and is used for the subsequent binning process.

The x",y" position data is used to obtain an energy correction factor from an energy correction lookup table 60. The event energy signal e" is multiplied by the energy correction factor in a multiplier 62 to produce a corrected energy value e'. The corrected energy value e' is then multiplied by a gain correction factor $C_g$ to produce a corrected energy value $C_g e'$. The corrected energy value $C_g e'$ is windowed by a window discrimination table 66 to produce the detector output energy value E.

The energy values E are accumulated over a period of time to assemble a histogram by detector SBC 70. The detector SBC 70 in a constructed embodiment is a single board computer which performs various processing tasks such as assembling a histogram from event data. The histogram is assembled continuously during acquisition and old data of the histogram is updated periodically by a decay-based scheme in which old data is weighted by a time constant representing refresh rate (e.g., 10 seconds) which is user configurable. The detector SBC 70 produces an autopeak gain adjustment $G_{AP}$ as described below, which is stored in a gain register 68. The gain register 68 may store other gain values G which are used in combination with the autopeak gain adjustment factor to produce the gain correction factor $C_g$.

Figure 4:
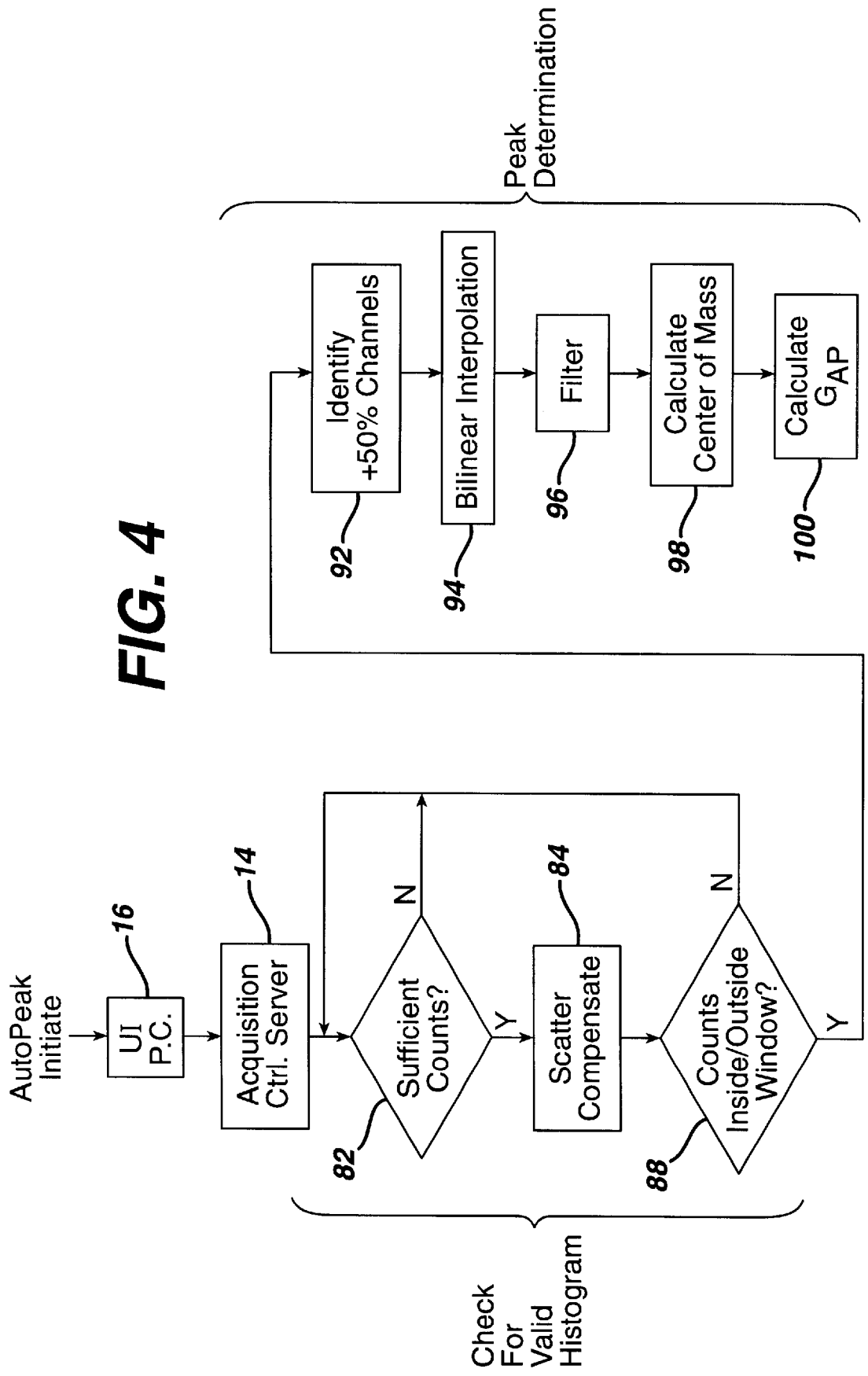
FIG. 4 is a flowchart illustrating autopeaking in accordance with a preferred embodiment of the present invention.

Referring to FIG. 4, the operation of a constructed embodiment of the present invention is described with reference to several of the other drawings. Automatic adjustment of the energy spectrum, referred to herein as autopeaking, may be done in several ways. One way is to enable the user to invoke autopeaking any time he or she desires by depressing a button or other control. Another way is for autopeaking to be carried out periodically as a regularly scheduled event during gamma camera operation. Yet another way is for autopeaking to be carried out as a constantly recurring background process whenever the presence of an isotope is detected. In the present example autopeaking is initiated by the user who selects or clicks on an "AutoPeak" softkey on the user interface display. As shown at the start of the flowchart of FIG. 4, this initiation of the AutoPeak process causes the UI P.C. 16 to issue an AutoPeak command over the Ethernet links 22c,22b to the acquisition control server 14. The control server 14 in turn sends an AutoPeak command over the Ethernet links 22b,22a to the detector SBC 70, as indicated by the AP input to the SBC 70. The remaining steps in the flowchart of FIG. 4 are carried out by the SBC 70 in the described constructed embodiment.

In addition to providing the camera operator with a means for initiating an AutoPeak adjustment, the UI P.C. 16 may be used to enable the camera operator to set various operating parameters of autopeaking. For example the operator may be able to set the period of time during which a spectrum is acquired. The histogram may be acquired then refreshed every 30 or 60 seconds, for instance. The operator may be able to set the resolution to which the spectral peak is identified by setting the number of bins in the energy spectrum. The operator may be able to set the minimally acceptable ratio of the energy peak to the background energy above which an identified spectral peak will be accepted, thereby preventing adjustment when no isotopes are present. The operator may also be able to set the range of incremental adjustments which the system will accept; very small adjustments to the signal gain are often unnecessary, and very large calculated adjustments (e.g., 5% or 10%) are an indication that the data on which the adjustment was calculated is unreliable. In such cases, no autopeaking adjustment will be made, but the system will acquire a new spectrum and perform another adjustment calculation.

Hence, the autopeaking program in the SBC begins by checking the validity of the histogram data. In step 82 the process checks to see whether sufficient counts are present on which to base a calculation. If no isotope is present in the camera, for instance, insufficient counts would be present and no autopeaking should be performed. The number of counts against which this check is performed may be set by the factory, or may be a user adjustable value within certain limits. If the answer to this check is "No," the process awaits a new histogram and then repeats the check.

Figure 5:
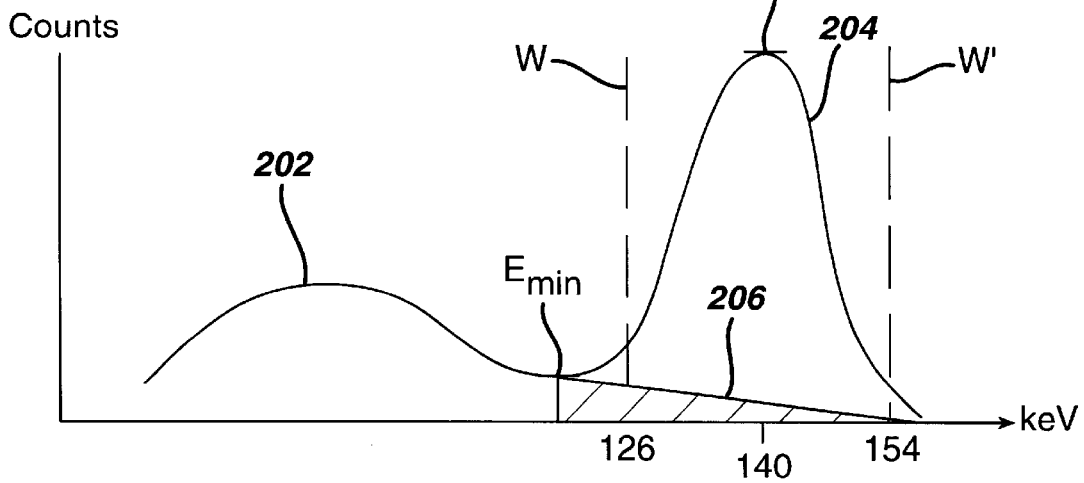
FIGS. 5, 6 and 7 illustrate histogram spectra used to explain the operation of the preferred embodiment of the present invention.

If the answer is "Yes," the process performs scatter compensation in step 84. The scatter compensation may be performed at any point in the validity checking process. A preferred technique for scatter compensation is shown in FIG. 5. An energy spectrum 202 is shown, with a pronounced photopeak 204 at approximately 140 keV. This spectrum may be contaminated by Compton scattering from the higher energy levels. One way to compensate for this unwanted scattering is to detect the minimum energy level of the spectrum which is shown as $E_{min}$. As greater scattering is experienced the $E_{min}$ level counts will increase. A linear plot is made from the $E_{min}$ level to the zero level termination of the photopeak 204 as shown by the shaded area 206. The counts in the respective channels covered by the shaded area 206 are deducted from the total counts in those channels to compensate for scattering in the photopeak 204 to a first approximation.

The next step in the preferred process is to assess the ratio of counts of the photopeak to the counts of the rest of the energy spectrum as shown at step 88. For instance FIG. 5 shows the photopeak 204 located in a window W–W' of the histogram. The window shown in the drawing is a 20% window ranging from 126 keV to 154 keV on either side of the nominal 140 keV center. The total counts within the window W–W' are compared to the total counts outside this window to determine whether a valid photopeak has been identified.

Figure 6:
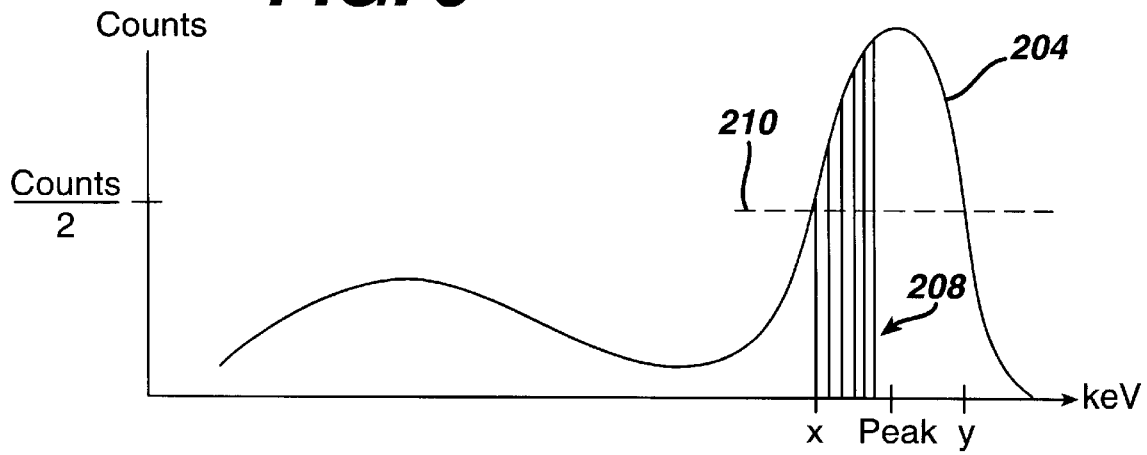

If the results of these histogram and photopeak validity checks are all "Yes," the process continues to determine the energy peak of the histogram and compares the measured peak with the theoretical peak for the isotope or isotopes present. The process of the preferred embodiment begins at step 92 by identifying the channels of the photopeak 204 having counts above the 50% level. FIG. 6 shows this level 210 where it is seen that the upper portion of the photopeak 204 has a number of channels 208 between x and y on the energy spectrum which exceed the Counts/2 level. A bilinear interpolation is performed on these channels in step 94 to increase the channel density and the resolution of the determination. The count data is then filtered in step 96 to reduce noise. A preferred filter is a boxcar filter which is a moving average filter exhibiting a rectangular filter function in the space domain. The peak of the spectrum is then determined in step 98 by performing a center of mass calculation on the filtered data. A preferred calculation is of the form $$PeakkeV = \frac{\sum_{k=x}^{y}(keV_k * Counts_k)}{\sum_{k=x}^{y} Counts_k}$$

An autopeaking gain correction factor $G_{AP}$ is then determined by the expression $$G_{AP} = \frac{E_{peak}(theoretical)}{PeakkeV}$$

As an example, for the isotope Tc99m the theoretical peak energy is 140.511 keV. If the above calculation found PeakkeV to be 142 keV, the factor $G_{AP}$ would be 0.9895. This gain factor is then used to scale every energy value produced by the detector. The gain adjustment is therefore used as a global correction factor for the particular detector. The gain factor is applied to every energy value from the detector including those of all isotopes used in the study. This means that the correction factor calculated from the principal energy peak of one isotope will effectively provide a correction factor for all isotopes used in the study.

It will be appreciated that the foregoing expression for $G_{AP}$ is calculated from a priori knowledge by the camera of a theoretical characteristic of an isotope present, namely, its nominal energy peak. This means that the autopeaking processor must know the isotopes being used in the study and their peaks. In the constructed embodiment the camera is informed by the operator as to the isotopes being used in the study, the location of the peaks of those isotopes, and the decay percentage of each isotope. The camera makes use of this information in the calculation of the gain factor for autopeaking.

Figure 7:
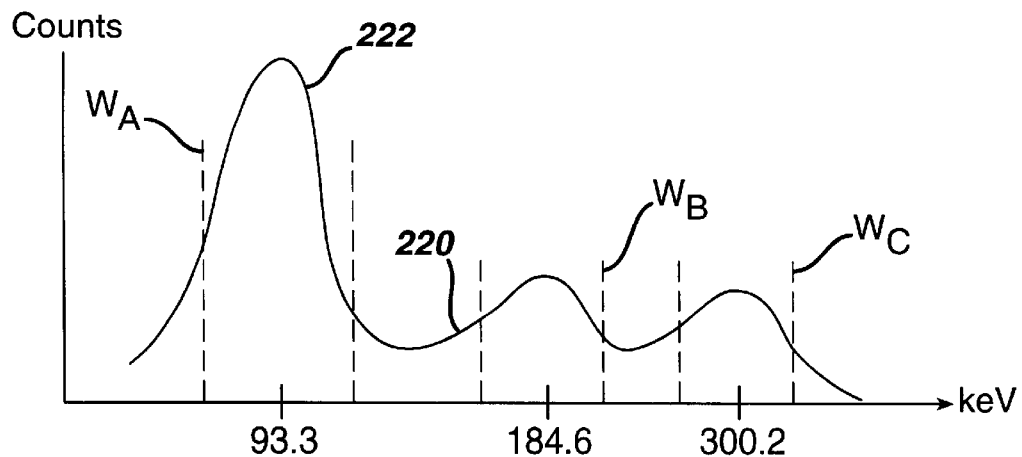

The peaks in the spectrum will vary with the type of isotope used in a particular study and also the number of isotopes used. For example, FIG. 7 illustrates a spectrum 220 with three peaks bounded by windows $W_A$, $W_B$, and $W_C$. The maximum photopeak the identified at 222 and in this example is the photopeak at the lowest energy level, 93.3 keV. In a preferred embodiment the autopeaking system always operates on the photopeak with the highest decay percentage, which is photopeak 222 in this example. The preferred embodiment makes maximum use of the dynamic range of the energy spectrum by scaling the energy levels to the center of the highest energy window. For instance, a 12-bit system has a maximum value of 4096. In the preferred embodiment when 12-bit resolution is used the gain of the detector is scaled so that the center of the highest energy window is scaled to a digital value of 1500 (decimal). In the example of FIG. 7 the 300.2 keV center of window $W_C$ is set at a value of 1500, and the other energy levels of the spectrum are scaled accordingly. The 184.6 keV center of window $W_B$ is scaled to (1500*184.6)/300.2, and the 93.3 keV center of window $W_C$ is scaled to (1500*93.3)/300.2.

In a study using multiple isotopes, the situation may be complicated by the absence of information about the activity level for each isotope. Thus, simply using the decay percentages to determine which energy peak to use for determining the gain factor may produce an incorrect or ambiguous result. A technique for dealing with this situation is to first find the peak for each isotope with the highest decay percentage, using the a priori knowledge of the isotopes used in the study. Any theoretical peak that is less than 20% from any other theoretical peak for any of the isotopes used in the study is ignored. If no peaks fulfill this criterion, autopeak correction cannot be performed and the system informs the user of this fact. For each peak that does fulfill this criterion, a 20% energy window is set up for each peak. The peak with the most counts is then used to perform the autopeaking adjustment.

Thus it is seen that the spectrum of the detected signals can be adjusted for the entire gamma camera by a single adjustment based on an isotope with a single photopeak, multiple photopeaks, or several isotopes with multiple photopeaks. The single adjustment will adjust the camera for multiple isotopes. The adjustment can be done digitally as shown in the described embodiments or in the analog domain if analog circuitry is employed.

What is claimed is:

1. A gamma camera system comprising:
    a detector head comprising a plurality of scintillation event detectors;
    an image processor coupled to the detector and responsive to detected scintillation events for producing image signals;
    a display coupled to the image processor for displaying a gamma camera image; and
    an energy spectrum adjustment processor responsive to energy signals produced by a plurality of the scintillation event detectors which adjusts the response of the detector to detected scintillation events by providing a gain adjustment signal which modifies the gain applied to the energy signals.

2. The gamma camera system of claim 1, wherein the energy spectrum adjustment processor is responsive to a histogram of scintillation event data for producing the gain adjustment signal.

3. The gamma camera system of claim 2, wherein the energy spectrum adjustment processor further comprises an energy peak detector which detects the peak energy of a photopeak of the histogram.

4. The gamma camera system of claim 3, further comprising a maximum photopeak detector which detects the highest photopeak of a histogram containing a plurality of photopeaks.

5. The gamma camera system of claim 4, wherein the detector head is responsive to scintillation events produced by a plurality of isotopes during a single nuclear medicine study.

6. The gamma camera system of claim 2, wherein the energy spectrum adjustment processor further comprises a validation processor for assessing the presence of valid histogram event data.

7. The gamma camera system of claim 1, further comprising a source of isotope characteristic data, wherein the energy spectrum adjustment processor is responsive to the isotope characteristic data.

8. The gamma camera system of claim 1, further comprising an autopeaking user control which is responsive to user action to produce an autopeaking initiation signal, wherein the energy spectrum adjustment processor acts to adjust the response of the detector to detected scintillation events in response to the autopeaking initiation signal.

9. A method for adjusting the response of a nuclear camera comprising:
    acquiring a histogram of event data from a plurality of scintillation event detectors of a nuclear camera detector head;
    analyzing the histogram to determine its validity;
    analyzing a photopeak of the histogram to determine its energy peak; and using the determined energy peak to adjust the response of the detector to detected scintillation events.

10. The method of claim 9, wherein analyzing the histogram comprises at least one of:
   analyzing the number of counts of the histogram;
   analyzing the energy peak signal to background ratio of a photopeak of the histogram; and
   analyzing the number of counts in an energy window of the histogram.

11. The method of claim 9, wherein analyzing a photopeak further comprises determining the energy peak by a center of mass calculation.

12. The method of claim 11, wherein analyzing a photopeak further comprises filtering count data of the photopeak.

13. The method of claim 9, wherein analyzing a photopeak further comprises identifying the maximum peak of a plurality of photopeaks.

14. The method of claim 13, wherein analyzing a photopeak further comprises identifying the maximum peak of a plurality of photopeaks produced in response to detection of events from a plurality of isotopes.

15. The method of claim 9, wherein using the determined energy peak comprises producing a gain adjustment value.

16. The method of claim 15, wherein producing a gain adjustment value comprises using the determined energy peak in combination with a theoretical energy peak value.

17. The method of claim 9, wherein acquiring a histogram comprises acquiring event data from a plurality of photomultiplier tubes.

18. The method of claim 9, wherein acquiring a histogram is performed periodically on a continuous basis.

19. The method of claim 18, wherein the steps of acquiring and using the determined energy peak are performed in response to a user-initiated command signal.

* * * * *